United States Patent [19]
Lewenstam et al.

[11] Patent Number: 5,584,979
[45] Date of Patent: Dec. 17, 1996

[54] ION-SELECTIVE ELECTRODE AND PROCEDURE FOR PRODUCING AN ION-SELECTIVE ELECTRODE

[75] Inventors: Andrzej Lewenstam, Helsinki; Johan Bobacka, Espoo; Ari Ivaska, Turku, all of Finland

[73] Assignee: Kone Instruments Oy, Espoo, Finland

[21] Appl. No.: 449,736

[22] Filed: May 25, 1995

[30] Foreign Application Priority Data

May 27, 1994 [FI] Finland .................................. 942510

[51] Int. Cl.⁶ .................................. G01N 27/26
[52] U.S. Cl. ................... 204/418; 204/403; 204/415; 422/82.03
[58] Field of Search .................. 204/418, 415, 204/403; 422/82.03; 257/253

[56] References Cited

U.S. PATENT DOCUMENTS

| | | | |
|---|---|---|---|
| 4,973,394 | 11/1990 | Ross et al. | 204/418 |
| 5,244,562 | 9/1993 | Russell | 204/418 |

FOREIGN PATENT DOCUMENTS

| | | |
|---|---|---|
| 2207250 | 1/1989 | United Kingdom . |
| WO87/01454 | 3/1987 | WIPO . |
| WO92/01219 | 1/1992 | WIPO . |

OTHER PUBLICATIONS

Nikolskii et al, Ion–Selective Electrode Rev., vol. 7, pp. 3–39 (1985) No month available.

Cattrall et al, Analytical Chemistry, vol. 43, No. 13, pp. 1905–1906 (Nov. 1971).

Buck, Ion–Selective Electrodes in Analytical Chemistry, vol. 1, pp. 58–63 Henry Freiser (Ed.), Plenum Press, NY (1978) No month available.

Cadogan et al, Analytical Chemistry, vol. 64, No. 21, pp. 2496–2501 (Nov. 1992).

Jen et al, Polym. Mater. Sci. Eng., vol. 53, pp. 79–83 (1985) No month available.

Cao et al, Synthetic Metals, vol. 48, pp. 91–97 (1992) No month available.

Audebert et al, Synthetic Metals, vol. 53, pp. 251–262 (1993) No month available.

Le Moigne et al, Makromol. Chem., vol. 192, pp. 515–530 (1991) No month available.

Yamamoto et al, J. Chem. Soc., Chem. Commun., pp. 797–798 (1993) No month available.

Nalwa, Synthetic Metals, vol. 35, pp. 387–391 (1990) No month available.

Bohnen et al, Makromol. Chem., vol. 192, pp. 1679–1693 (1991) No month available.

WO 92/01219 Jan. 23, 1992.

WO 87/01454 Mar. 12, 1987.

*Primary Examiner*—Bruce F. Bell
*Attorney, Agent, or Firm*—Birch, Stewart, Kolasch & Birch, LLP

[57] ABSTRACT

The invention relates to an ion-selective electrode and to a procedure for producing the electrode. The electrode is a single-piece all-solid-state electrode comprising a conducting or semiconducting solid substrate (6) coated with a composite membrane (4). The electrode is produced by dissolving a conjugated polymer or oligomer together with the components of a conventional ion-selective membrane to produce a solution, applying this solution to an electronically conducting or semiconducting substrate and allowing the solvent to evaporate, with the result that a composite membrane is formed on the substrate.

23 Claims, 1 Drawing Sheet

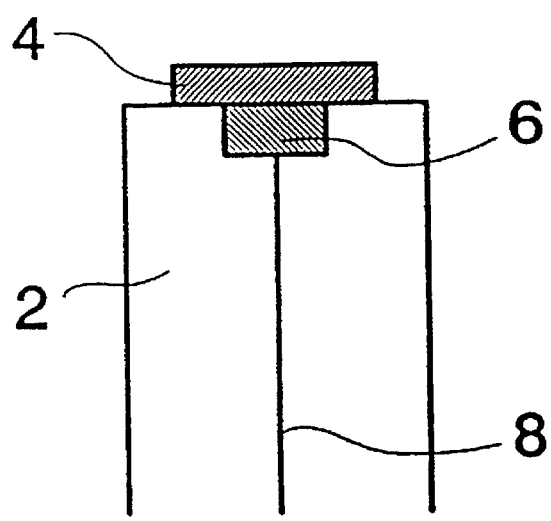
FIG.

2

ION-SELECTIVE ELECTRODE AND PROCEDURE FOR PRODUCING AN ION-SELECTIVE ELECTRODE

FIELD OF THE INVENTION

The present invention relates to an ion-selective electrode and to a procedure for producing an ion-selective electrode.

BACKGROUND OF THE INVENTION

The construction of so called conventional ion-selective electrodes (ISE) employing different ion-selective membranes can be depicted by the following scheme:
Examined solution | Ion-selective membrane | Reference solution | Reference element
where the vertical bar represents an interface between two phases. In this conventional type of ISE the ion-selective membrane is in electrical contact with the reference solution, depending on the ion-exchange equilibrium. The reference element is in electronic contact with the external electronic instrumentation. The transfer from ionic conductivity (in the membrane and the reference solution) to electronic conductivity (in the reference element and external instrumentation) is provided by the reversible electrode reaction of the reference element. By a proper choice of the reference element and the composition of the reference solution it is possible to obtain an ISE with a stable and reproducible standard potential [1].

In some applications it is advantageous to replace the reference solution by a solid contact giving an all-solid-state ISE [1]. One such approach is to attach the ion-selective membrane directly to a solid, electronically conductive substrate as represented by the following scheme [2]:
Examined solution | Ion-selective membrane | Substrate This type of ISE, hereinafter referred to as the coated-wire electrode (CWE), can be fabricated in various shapes and sizes. It can be miniaturized, and it may be inexpensive to produce since the substrate does not necessarily have to be a noble metal. However, irreproducibility and drift of the electrode potential are a problem usually encountered with the CWE. The instability of the potential may be caused by the blocked interface between the ionically conducting ion-selective membrane and the electronically conducting substrate [3].

Several approaches to improve the potential stability of the CWE have been tried [1]. One such approach is to connect the ion-selective membrane to the solid substrate via an intermediate layer having mixed ionic-electronic conductivity, as represented by the following scheme:
Examined solution | Ion-selective membrane | Intermediate layer | Substrate In this type of ISE, hereinafter referred to as the solid-contact ISE (SCISE), the transfer from ionic to electronic conductivity is possible due to the mixed ionic-electronic conductivity of the intermediate layer. The ion-selective membrane is in ionic equilibrium with the intermediate layer, which is in electronic equilibrium with the substrate [1]. Doped conjugated polymers like p-type polypyrrole can be regarded as mixed ionic-electronic conductors an they can be used as an intermediate layer in the SCISE [4].

The main advantage of using an intermediate layer between the ion-selective membrane and the substrate is to improve the stability of the electrode potential, i.e. SCISEs are more stable than CWEs. However, due to the need for an intermediate layer, SCISEs are more complicated to fabricate than CWEs.

Another approach to improve the potential stability of the CWE is to incorporate an oxidable and reducible substance, a so-called redox agent in the ion-selective membrane, as represented by the following scheme[1]:
Examined solution | Ion-selective membrane | Redox agent | Substrate In this type of ISE, hereinafter referred to as the redox-loaded electrode (RLE), electronic equilibrium exists between the redox agent in the membrane and the electronically conducting substrate, resulting in improved stability of the electrode potential as compared to the CWE. In some cases, however, the RLE shows potential drift due to dissolution of the redox agent in the membrane [1]. In other cases the life time of the electrode is short due to disintegration of the membrane phase. Depending on the amount and quality of the redox agent in the membrane, there is also the risk that the RLE will be redox sensitive due to the possibility of electron transfer at the membrane-solution interface.

In the present invention, an electronically conducting or semiconducting conjugated polymer is mixed with an ion-selective membrane, resulting in a novel type of single-piece all-solid-state ion-selective electrode (SPE).

SUMMARY OF THE INVENTION

The present invention is based on the discovery that conjugated polymers soluble in certain organic solvents can be incorporated in conventional ion-selective polymer membranes, resulting in a composite membrane. The electrode of the invention is characterized by the features presented in the characterization part of claim 1. The procedure of the invention is characterized by the features presented in the characterization part of claim 7. Preferred embodiments of the invention are defined in the subclaims.

When a conducting substrate is coated with a composite membrane, the result is a novel type of single-piece all-solid-state ion-selective electrode (SPE). The conducting or semiconducting conjugated polymer produces some electronic conductivity in the composite membrane. Therefore, electron transfer can take place at the composite membrane-substrate interface. Since the composite membrane is in electronic equilibrium with the substrate, the standard potential of the SPE can be more stable than that of the CWE. When an undoped or a lightly doped conjugated polymer is used in its semiconducting state, the SPE does not show any redox sensitivity.

BRIEF DESCRIPTION OF THE DRAWINGS

The FIGURE shows an SPE in a schematic form.

DESCRIPTION OF THE INVENTION

In the following, the invention is described in detail by the aid of examples and by referring to the FIGURE in the drawing, presenting a diagram representing the electrode of the invention.

In the present invention, a conjugated polymer is mixed with an ion-selective membrane, resulting in a novel type of single-piece all-solid-state ion-selective electrode (SPE), which is represented by the following scheme:
Examined solution | Ion-selective membrane | Conjugated polymer | Substrate An ion-selective membrane containing a conjugated polymer will hereinafter be referred to as a composite membrane to distinguish it from a conventional ion-selective membrane. An electronically conducting or semiconducting substrate coated with such a composite membrane will hereinafter be referred to as a SPE.

The FIGURE shows a SPE in a schematic form. The electrode frame 2 is made e.g. of teflon. Fitting on it is a solid substrate 6 made of platinum, gold or carbon. By means of an electric conductor 8, the substrate is connected to an external measuring circuit or equivalent (not shown). A composite membrane 4 as provided by the invention is formed on the substrate on the end of the electrode frame. As noted above, the FIGURE only presents an example of the electrode, but its implementations may vary greatly both in respect of structure, form and materials.

In this type of SPE, the conjugated polymer functions as an electronic conductor or semiconductor and electronic equilibrium can prevail at the composite membrane-substrate interface. The electronic conductivity of the conjugated polymer can be varied by varying the doping level in a manner known to the person skilled in the art. As an alternative to the polymer, an oligomer can also be used. At low levels of doping, the conjugated polymer has semiconducting properties and it is then important to choose a substrate material that gives an ohmic contact at the composite membrane-substrate interface. By using a conjugated polymer that is soluble in the same solvent as the other membrane components, this type of SPE can be prepared by a one-step dipping process. The use of a soluble conjugated polymer also allows an effective mixing of the conjugated polymer in the composite membrane phase.

More specifically, a SPE may be produced by dissolving a soluble semiconducting organic polymer, e.g. poly(3-alkylthiophene) [5], and the components used for a conventional ion-selective membrane, e.g. ionophore or ion-exchanger with a plasticizer and polyvinyl chloride (PVC) and a lipophilic salt (optional) in a common solvent, e.g. tetrahydrofuran (THF). This composite solution is then applied on the substrate, e.g. platinum, gold or carbon, and the solvent is evaporated, with the result that a composite membrane of a thickness of e.g. about 0.15 mm is formed on the substrate. The amount of poly(3-alkylthiophene) in the composite membrane may vary, being e.g. less than 50% by weight.

Poly(3-alkylthiophene)s are conjugated polymers that have been extensively investigated in recent years. Poly(3-alkylthiophene)s with alkyl chains longer than three carbon atoms are soluble in organic solvents, e.g. tetrahydrofuran (THF) or chloroform ($CHCl_3$). In their lightly doped (unintentionally doped) state, poly (3-alkylthiophene)s are p-type semiconductors expected to form an ohmic contact with materials having high work functions, eg. platinum, gold or carbon.

The following examples illustrate the invention.

EXAMPLE 1

Chemically synthesized poly(3-octylthiophene) (POT), (a commercial product e.g. by Neste Oy) was dissolved in tetrahydrofuran (THF) at room temperature by stirring and the insoluble fractions were removed by filtering. The soluble POT was used for further experiments (after evaporation of THF). All experiments were conducted at a temperature of 23°±2° C.

A single-piece lithium-selective electrode (Li-SPE) was produced in the following way. POT dissolved in THF was mixed with a neutral carrier (ETH 2137, 5-butyl-5-ethyl-N,N,N',N'-tetracyclohexyl-3,7-dioxaazelaic diamide), lipophilic salt, plasticizer and PVC, all dissolved in THF. This composite solution was applied on a glassy carbon disc electrode (area=0.07 $cm^2$) and the solvent was evaporated at room temperature for at least 5 hours. This resulted in a composite membrane (total mass approximately 12.3 mg, thickness approximately 0.15 mm) on the glassy carbon substrate, giving a single-piece lithium-selective electrode (Li-SPE). The concentration of POT in the composite membrane was 5, 10, 15, 20 or 25% (by weight).

Several Li-SPEs prepared as described above were conditioned for at least 12 hours in an aqueous solution containing $10^{-1}$M LiCl. After the conditioning, the Li-SPEs were used as indicator electrodes and the potential versus a Ag/AgCl/Ci(3M) reference electrode was measured in aqueous solutions containing different concentrations of LiCl ($10^{-1}$–$10^{-6}$) using $10^{-1}$M $KNO_3$ as background electrolyte. The potentiometric selectivity coefficients $K_{ij}^{pot}$, where $i=Li^+$ and $j=Na^+$, $K^+$ or $NH_4^+$, for the Li-SPE were determined by the "separate solution method" ($C_i=C_j=0.01M$, background salt was either 0.1M $KNO_3$ or 0.1M $NH_4NO_3$). The response characteristics of Li-SPEs containing different amounts of POT are shown in Table 1. The response time was less than 15 seconds (concentration step from $10^{-3}$ to $10^{-2}$ LiCl under magnetic stirring). The electrode did not show any hysteresis in the concentration range studied. Neither did the electrode give any redox response for the mixture 0.1M LiCl+1 mM redox couple ($Fe(CN)_6^{3-}$/$Fe(CN)_6^{4-}$), in which the concentration ratio of the redox couple was changed.

The stability of the electrode potential was studied using a Li-SPE containing 15% POT. The electrode was kept in 0.1M LiCl solution containing 0.1M $KNO_3$ as background salt for eight days and the electrode potential was measured during this period. After an initial conditioning time of 3 days, the potential of the Li-SPE drifted by only ca. 0.8 mV/day.

TABLE 1

| [POT]/ | Slope mV/ | Detection limit / | $logK_{ij}^{pot}$ | | |
|---|---|---|---|---|---|
| % (/w) | dec | M | $j = Na^+$ | $j = K^+$ | $j = NH_4^+$ |
| 5 | 56.0 | $2.6 \times 10^{-4}$ | −1.27 | −1.29 | −1.39 |
| 10 | 56.8 | $1.7 \times 10^{-4}$ | −1.31 | −1.46 | −1.49 |
| 15 | 57.8 | $1.8 \times 10^{-4}$ | −1.40 | −1.48 | −1.61 |
| 20 | 55.5 | $1.6 \times 10^{-4}$ | −1.37 | −1.47 | −1.57 |
| 25 | 56.8 | $1.8 \times 10^{-4}$ | −1.40 | −1.47 | −1.62 |

EXAMPLE 2

A single-piece chloride-selective electrode (Cl-SPE) was produced according to the same principle as described in EXAMPLE 1 for the Li-SPE. POT dissolved in THF was mixed with ion-exchanger (methyltridodecylammonium chloride), plasticizer and PVC, all dissolved in THF. This composite solution was applied on a glassy carbon disc electrode (area=0.07 $cm^2$) and the solution was evaporated at room temperature for at least 5 hours. This resulted in a composite membrane (total mass approximately 11.7 mg) on the glassy carbon substrate, giving a Cl-SPE. The concentration of POT in the composite membrane was 5, 10 or 15% (by weight).

The Cl-SPEs, prepared as described above, were conditioned for at least 12 hours in an aqueous solution containing $10^{-1}$M KCl. After the conditioning, the Cl-SPEs were used as indicator electrodes and the potential versus a Ag/AgCl/KCl(3M) reference electrode was measured in aqueous solutions containing different concentrations of KCl ($10^-$ $1-10^{-7}$M). The slope of the calibration curves for Cl-SPE containing 5% POT was −54.6 mV/decade and for Cl-SPE containing 15% POT, −54.9 mV/decade.

The stability of the electrode potential was studied by measuring the potential of the Cl-SPEs in 0.1M KCl solution during a period of 17 days. After an initial conditioning time of 8 days, the potential of the Cl-SPE containing 5% POT drifted by only ca. 1.4 mV/day. The potential of the Cl-SPE containing 15% POT drifted by ca. 1.0 mV/day.

BIBLIOGRAPHY

1. B. P. Nikolskii and E. A. Materova, Ion-Selective Electrode Rev., 7, s. 3–39 (1985)
2. R. W. Cattrall and H. Freiser, Anal. Chem., 43, s. 1905∝1906 (1971)
3. R. P. Buck, in Ion Selective Electrodes in Analytical Chemistry, H. Freiset (ed), Plenum, New York, Vol. 1, s. 58–63 (1978)
4. A. Cadogan, Z. Gao, A. Lewenstam, A. Ivaska and D. Diamond, Anal. Chem., 64, s. 2496–2501 (1992)
5. K. Y. Jen, R. Oboodi and R. L. Elsenbaumer, Polym. Mater. Sci. Eng., 53, s. 79–83 (1985)

We claim:

1. An ion-selective electrode comprising a conducting or semiconducting solid substrate and a composite membrane on said substrate, said composite membrane comprising (i) a first polymer, (ii) a plasticizer, (iii) an ionophore or ion-exchanger, and (iv) an oligomer or a second polymer, said oligomer or second polymer being an electronically conducting or semiconducting conjugated oligomer or polymer, respectively.

2. The electrode as defined in claim 1, wherein the conjugated polymer is selected from polythiophenes, polypyrroles, polyanilines, and combinations thereof.

3. The electrode as defined in claim 2, wherein said second polymer is a poly(3-alkyl-thiophene).

4. The electrode as defined in claim 3, wherein said alkyl group contains at least four carbon atoms.

5. The electrode as defined in claim 4, wherein said second polymer is poly(3-octylthiophene).

6. The electrode as defined in claim 3, wherein said poly(3-alkyl-thiophene) is contained in said membrane in an amount of from 5% to 50% by weight.

7. The electrode as defined in claim 6, wherein said poly(3-alkyl-thiophene) is contained in said membrane in an amount of from 5% to 25% by weight.

8. The electrode as defined in claim 2, wherein said second polymer is a polyaniline.

9. The electrode as defined in claim 1, wherein the conjugated oligomer comprises repeating units of thiophenes, pyrroles, anilines or combinations thereof.

10. The electrode as defined in claim 1, wherein said ion-selective membrane further comprises a lipophilic salt.

11. The electrode as defined in claim 10, wherein the conjugated polymer is polythiophenes, polypyrroles, polyanilines, or combinations thereof.

12. The electrode as defined in claim 10, wherein the conjugated oligomer comprises repeating units of thiophenes, pyrroles, anilines or combinations thereof.

13. The electrode as defined in claim 1, wherein said second polymer is soluble in an organic solvent.

14. The electrode as defined in claim 1, wherein said first polymer is poly(vinyl chloride).

15. The electrode as defined in claim 1, wherein said substrate is carbon.

16. A process for preparing an ion-selective electrode, which comprises the steps of:

(1) dissolving a polymer, a plasticizer, an ionophore or ion-exchanger, and a conjugated polymer or oligomer in an organic solvent to produce a solution;

(2) applying this solution to an electronically conducting or semiconducting substrate; and (3) allowing the solvent to evaporate, with the result that a composite membrane is formed on the substrate.

17. The process as defined in claim 16, wherein the conjugated polymer is selected from polythiophenes, polypyrroles, polyanilines, and combinations thereof.

18. The process as defined in claim 16, wherein the conjugated oligomer comprises repeating units of thiophenes, pyrroles, anilines or combinations thereof.

19. The process as defined in claim 16, wherein the polymer is poly(vinyl chloride).

20. The process as defined in claim 19, wherein the conjugated polymer is selected from polythiophenes, polypyrroles, polyanilines, and combinations thereof.

21. The process as defined in claim 19, wherein the conjugated oligomer comprises repeating units of thiophenes, pyrroles, anilines or combinations thereof.

22. The process as defined in claim 16, wherein said organic solvent is tetrahydrofuran.

23. The process as defined in claim 16, wherein said composite membrane has a thickness of about 0.15 mm.

* * * * *